US010568506B2

(12) United States Patent
Thibault et al.

(10) Patent No.: US 10,568,506 B2
(45) Date of Patent: Feb. 25, 2020

(54) OPTICAL FIBER-BASED SPECTROREFLECTOMETRIC SYSTEM

(71) Applicant: ZILIA INC., Quebec (CA)

(72) Inventors: Simon Thibault, Quebec (CA); Denis Brousseau, Levis (CA); Dominic Sauvageau, Edmonton (CA)

(73) Assignee: ZILIA INC., Quebec (CA)

( * ) Notice: Subject to any disclaimer, the term of this patent is extended or adjusted under 35 U.S.C. 154(b) by 0 days.

(21) Appl. No.: 16/473,238

(22) PCT Filed: Dec. 22, 2017

(86) PCT No.: PCT/CA2017/051587
§ 371 (c)(1),
(2) Date: Jun. 24, 2019

(87) PCT Pub. No.: WO2018/112660
PCT Pub. Date: Jun. 28, 2018

(65) Prior Publication Data
US 2019/0320893 A1  Oct. 24, 2019

Related U.S. Application Data

(60) Provisional application No. 62/437,984, filed on Dec. 22, 2016.

(51) Int. Cl.
*A61B 3/15* (2006.01)
*A61B 3/00* (2006.01)
(Continued)

(52) U.S. Cl.
CPC . *A61B 3/12* (2013.01); *A61B 3/14* (2013.01)

(58) Field of Classification Search
CPC .. A61B 3/12; A61B 3/14; A61B 3/158; A61B 3/152; A61B 3/0008
See application file for complete search history.

(56) References Cited

U.S. PATENT DOCUMENTS 6,347,242 B1   2/2002  Friedlander
6,416,481 B2   7/2002  Faubert et al.
(Continued)

FOREIGN PATENT DOCUMENTS

CA   2323434 C    5/2009
EP   1065968 B1   3/2007

OTHER PUBLICATIONS

International Search Report and Written Opinion of PCT/CA2017/051587 dated Apr. 9, 2018, 7 pages.

*Primary Examiner* — Jack Dinh
(74) *Attorney, Agent, or Firm* — Workman Nydegger

(57) ABSTRACT

A spectroreflectometric system for performing a spectral analysis on the fundus of a patient's eye is provided. The system projects probing light towards the fundus of the eye and collects return light representative of an image of the fundus. An interface module positioned at a sensing interface at an image plane of the fundus is provided and includes an optical fiber light collector having a collector input extending along the sensing interface for collecting the return light, and a collector output connectable to an imaging device. The interface module further includes at least one extraction optical fiber having a fiber input extending at the sensing interface and a fiber output connectable to a spectral analyser. The fiber input is integrated into the collector input so as to collect a portion of the return light corresponding to an analysis area within the image of the fundus.

20 Claims, 6 Drawing Sheets

(51) Int. Cl.
*A61B 3/12* (2006.01)
*A61B 3/14* (2006.01)

(56) References Cited

U.S. PATENT DOCUMENTS 7,896,498 B2 3/2011 Munger et al.
2002/0151774 A1 10/2002 Soller et al.

OPTICAL FIBER-BASED SPECTROREFLECTOMETRIC SYSTEM

TECHNICAL FIELD

The technical field generally relates to devices for oximetry or other eye-related measurements and more particularly concerns an optical fiber-based spectroreflectometric system.

BACKGROUND

Ocular oximetry, that is, the measurement of the degree of oxygen saturation of blood in tissues of the eye, is a useful non-invasive tool with widespread medical and health monitoring applications. Indeed, measurement of oxygen in biological tissues can provide valuable information on metabolism, responses to stress, the pathophysiology of different illnesses and conditions or the efficacy of administered treatments.

Spectroreflectometric systems can be used to provide oximetric measurements or other information from the fundus of a patient's eye through a spectral analysis of light resulting from the interaction of illumination light with the fundus medium or features in the eye fundus. For optimal use in the field, oximeters or equivalent devices and systems should preferably be efficient, simple to use and easy to manufacture, Low cost and miniaturisation of such equipment are also factors of interest. A challenge in providing such features is in the proper design of the optical arrangement for image and data acquisition and signal redirection for analysis.

There remains a need for an improved device that can be used for ocular oximetry or the analysis of other parameters in a patient's eye that provide at least some of the above-mentioned advantages.

SUMMARY

In accordance with one aspect, there is provided a spectroreflectometric system for performing a spectral analysis on the fundus of a patient's eye, comprising:
  a light source generating probing light;
  a fundus probing assembly configured to project the probing light towards the fundus of the patient's eye and to collect return light representative of an image of the fundus;
  an imaging device for detecting and displaying the image of the fundus;
  a spectral analyser configured to perform said spectral analysis; and
  an interface module comprising:
  a sensing interface extending at an image plane of the fundus;
  an optical fiber light collector having a collector input extending along the sensing interface for collecting the return light, and a collector output connected to the imaging device;
  at least one extraction optical fiber, each of the at least one extraction optical fiber having a fiber input extending at the sensing interface and a fiber output connected to the spectral analyser, the fiber input being integrated into the collector input so as to collect a portion of the return light corresponding to an analysis area within the image of the fundus.

The light source may for example include at least one LED emitter, and may be integrated into the fundus probing assembly. In one example, the fundus probing assembly may include one or more optical components configured to transfer the image of the fundus onto the image plane, an assembly of LED emitters defining the light source and a casing enclosing the one or more optical components and the assembly of light emitters.

In some implementations, the optical fiber light collector may include a plurality of coherent optical light guides each guiding a segment of the image of the fundus to the imaging device.

In some implementations, the optical fiber light collector may include an optical fiber bundle including a plurality of optical fiber links, the optical fiber links having coplanar fiber endfaces collectively defining the collector input. The collector interface may be provided with a slit extending across the fiber endfaces between a peripheral entry point and an interior exit point, the extraction fiber lying within the slit with the fiber input projecting through the interior exit point in a coplanar relationship with the fiber endfaces of the optical fiber links. Each of the at least one extraction optical fiber may be defined by a corresponding one of the optical fiber links.

In some implementations, the optical fiber light collector may include a plurality of optical fiber bundles assembled in a super-bundle. Each optical fiber bundle includes a plurality of optical fiber links, the optical fiber links of all of the fiber bundles having coplanar fiber endfaces collectively defining the collector input. Each of the extraction optical fibers may extend within the super-bundle.

In some implementations, the optical fiber collector may include a large multimode optical fiber having a fiber endface defining the collector input. The collector interface may be provided with a slit extending across the fiber endface of the large multimode optical fiber between a peripheral entry point and an interior exit point, the extraction fiber lying within this slit with the fiber input projecting through the interior exit point in a coplanar relationship with the fiber endface of the large multimode optical fiber.

In accordance with another aspect, there is further provided an interface module for use in a spectroreflectometric system for performing a spectral analysis on the fundus of a patient's eye. The system projects probing light towards the fundus of the patient's eye and collects return light representative of an image of the fundus. The interface module can be positioned at a sensing interface extending at an image plane of the fundus and includes:
  an optical fiber light collector having a collector input extending along the sensing interface for collecting the return light, and a collector output connectable to an imaging device;
  at least one extraction optical fiber, each of the at least one extraction optical fiber having a fiber input extending at the sensing interface and a fiber output connectable to a spectral analyser, the fiber input being integrated into the collector input so as to collect a portion of the return light corresponding to an analysis area within the image of the fundus.

In some implementations, the optical fiber light collector may include a plurality of coherent optical light guides each guiding a segment of the image of the fundus to the imaging device.

The optical fiber light collector may include an optical fiber bundle including a plurality of optical fiber links, the optical fiber links having coplanar fiber endfaces collectively defining the collector input. In some implementations, the collector interface is provided with a slit extending across the fiber endfaces between a peripheral entry point and an interior exit point, the extraction fiber lying within the slit with the fiber input projecting through the interior exit point in a coplanar relationship with the fiber endfaces of the optical fiber links.

In some implementations each of the at least one extraction optical fiber is defined by a corresponding one of the optical fiber links.

In other implementations, the optical fiber light collector includes a plurality of optical fiber bundles assembled in a super-bundle. Each optical fiber bundle includes a plurality of optical fiber links, the optical fiber links of all of the fiber bundles having coplanar fiber endfaces collectively defining the collector input. Each of the extraction optical fibers may extend within said super-bundle.

In some implementations, the optical fiber collector includes a large multimode optical fiber having a fiber endface defining the collector input. The collector interface may have a slit extending across the fiber endface of the large multimode optical fiber between a peripheral entry point and an interior exit point, the extraction fiber lying within said slit with the fiber input projecting through the interior exit point in a coplanar relationship with the fiber endface of the large multimode optical fiber.

It will be noted that the module above may be used in other applications than spectroreflectometry of the fundus of the eye. In accordance with another aspect, there is also provided an interface module for use in a system for performing a spectral analysis on a medium, the system projecting probing light towards the medium and collecting return or transmitted light representative of an image of the medium, the interface module being positionable at a sensing interface extending at an image plane of the medium and comprising:

an optical fiber light collector having a collector input extending along the sensing interface for collecting the return or transmitted light, and a collector output connectable to an imaging device;

at least one extraction optical fiber, each of the at least one extraction optical fiber having a fiber input extending at the sensing interface and a fiber output connectable to a spectral analyser, the fiber input being integrated into the collector input so as to collect a portion of the return light corresponding to an analysis area within the image of the medium.

In some implementations, the optical fiber light collector may include a plurality of coherent optical light guides each guiding a segment of the image of the medium to the imaging device.

The optical fiber light collector may include an optical fiber bundle including a plurality of optical fiber links, the optical fiber links having coplanar fiber endfaces collectively defining the collector input. In some implementations, the collector interface is provided with a slit extending across the fiber endfaces between a peripheral entry point and an interior exit point, the extraction fiber lying within the slit with the fiber input projecting through the interior exit point in a coplanar relationship with the fiber endfaces of the optical fiber links.

In some implementations each of the at least one extraction optical fiber is defined by a corresponding one of the optical fiber links.

In other implementations, the optical fiber light collector includes a plurality of optical fiber bundles assembled in a super-bundle. Each optical fiber bundle includes a plurality of optical fiber links, the optical fiber links of all of the fiber bundles having coplanar fiber endfaces collectively defining the collector input. Each of the extraction optical fibers may extend within said super-bundle.

In some implementations, the optical fiber collector includes a large multimode optical fiber having a fiber endface defining the collector input. The collector interface may have a slit extending across the fiber endface of the large multimode optical fiber between a peripheral entry point and an interior exit point, the extraction fiber lying within said slit with the fiber input projecting through the interior exit point in a coplanar relationship with the fiber endface of the large multimode optical fiber.

Other features and aspects of the invention will be better understood upon reading of embodiments thereof with reference to the appended drawings.

BRIEF DESCRIPTION OF THE DRAWINGS

FIG. 1A is an enlarged representation of the sensing interface of the system of FIG. 1.

DETAILED DESCRIPTION

The present description generally relates to spectroreflectometric systems for performing a spectral analysis on the fundus of a patient's eye.

In the context of the present application, the expression "spectroreflectometric" is generally used as a contraction of the terms "spectral" and "reflectometric" in reference to techniques related to spectral reflectometry. As readily understood by those skilled in the art, reflectometry refers to the use of light or other electromagnetic waves to analyse the properties of a medium. Light is typically projected towards the medium and the interactions of the light wavefront with the medium interface leads to the generation of return light having optical properties affected by the medium. In spectral reflectometry, a spectral analysis of the return light, that is, an analysis of the properties of the return light as a function of its wavelength profile, is used to obtain or deduce information about the medium and its composition.

Spectral reflectometry can be used in ophthalmologic contexts to sense oxygen levels in the fundus of the eye of a patient. By way of example, oxygen levels are assessed through the presence of oxyhemoglobin which has a characteristic light absorbance pattern. Similarly, the concentration of deoxyhemoglobin, and carboxyhemoglobin (related to the levels of carbon dioxide present) can be determined based on their respective light absorbance patterns. These parameters and their regulation are indicative of metabolism, responses to stress and stimuli and, potentially, pathophysiologies. It will however be understood that other molecules and phenomena may also be studied, inasmuch as they lead to alterations in the spectral profiles of reflected light. It will also be understood that the spectral analysis may be performed for different regions of the fundus of the patient's eye or on features present on the fundus. In other implementations, the spectral analysis may be performed on other portions of the eye such as the conjunctiva.

It will however be readily understood that the system described herein may be used for different applications than for the spectroreflectometric analysis of the eye. More broadly, the system below may be of use in any context where spectral information from a portion of an imaged medium is desired. One skilled in the art will readily understand that in some applications the system may be used to analyze light transmitted by a medium of interest. The medium under study may be other than the eye such as for example the skin, organ tissues, exposed muscle tissues, and other biological tissues.

Figure 1:
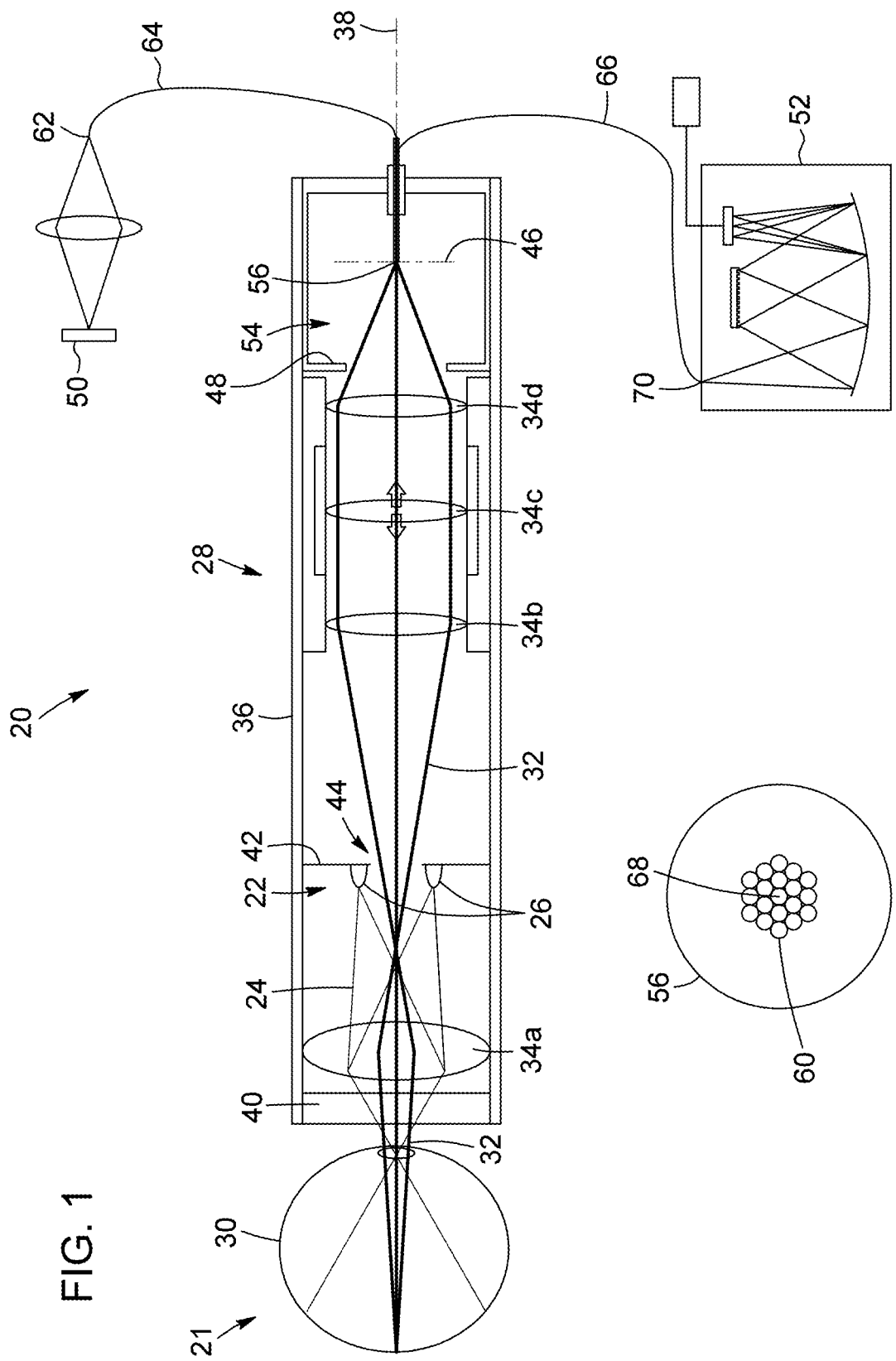
FIG. 1 is a schematized representation of a spectroreflectometric system according to one embodiment.

With reference to FIG. 1, there is shown a schematized representation of a spectroreflectometric system 20 for performing a spectral analysis on the fundus of a patient's eye 21 according to one embodiment.

The system 20 first includes a light source 22. In use, the light source 22 generates probing light 24. The expression "probing light" is used herein to refer to electromagnetic radiation suitable for projection into the eye of a patient and for inducing, producing or otherwise generating return light 32 which can yield information of interest on the fundus of the patient's eye upon suitable analysis. It will be readily understood that the term "light" is not considered limited to the visible portion of the electromagnetic spectrum. The probing light 24 preferably has a broadband spectral profile encompassing all the wavelengths of interest for the spectral analysis which the system is configured to perform. In some variants, the probing light may be white light. In other variants, the probing light 24 may have a spectral profile designed in view of the field of use of the system. In yet another set of variants, the probing light may have any other suitable spectral profile as dictated by one or more factors such as the optical properties of the patient's eye, the availability of light sources, the nature and characteristics of the spectral analysis to be performed, etc.

The light source 22 may include one or more LED (Light Emitting Diode) emitters. In the illustrated embodiment, the light source 22 for example includes an assembly of several LED emitters 26 mounted in a circular or other arrangement such that light beams emitted by the plurality of emitters 26 collectively define the probing light 24. The LED emitters of a given light source 22 may have similar optical properties or different complementary optical properties selected in order to obtain the desired optical properties of the probing light once combined. It will be readily understood that numerous other variants of light sources such as lasers, OLEDs, fluorescent, incandescent, tungsten, and other light bulbs may be used in alternative embodiments of the invention.

Still referring to FIG. 1, the system 20 further includes a fundus probing assembly 28 configured to project the probing light 24 towards the fundus 30 of the patient's eye 21 and to collect return light 32 representative of an image of the fundus 30.

As known in the art, the fundus of an eye probed with a multi-wavelength light beam will absorb specific wavelengths of light based on its composition. For example, oxyhemoglobin, deoxyhemoglobin, and carboxyhemoglobin have characteristics absorbance patterns which can be found in literature. In other variants, the light absorbance or transmission characteristics of other molecules in the eye or of specific molecules in other tissues may also be known from literature or may be predetermined experimentally.

It will be readily understood that the fundus probing assembly may be embodied by a variety of configurations suitable to the purpose of optically probing a patient's eye. The fundus probing assembly may include one or more optical components 34 configured to transfer the image of the fundus 30 onto an image plane 46. The optical components may include lenses, mirrors, beamsplitters, polarizers, filters, etc. The optical components may be arranged in any suitable fashion as is generally known to those skilled in the art. The fundus probing assembly 28 may further include other non-optical components such as mechanical or electrical components providing structural and/or functional support to the optical components such as fixed or displaceable mounts, screens, pinholes, step motors, etc.

In one implementation, the fundus probing assembly 28 may include a casing 36 enclosing the optical components 34 of the fundus probing assembly 28. The casing may be made of suitable rigid materials such as aluminum, plastic, glass fiber reinforced plastic and the like. The casing is preferably provided with a light passage allowing the probing light to travel out of the casing and the return light to travel back into the casing. The light passable may for example include an opening through the casing or an optical window 40, such as illustrated in FIG. 1. The optical window may be made of glass, a plastic material or any material which is transparent at least over the spectral range of the probing light and return light. The optical window may have an anti-reflection coating to avoid undesirable reflections or "ghosts".

Advantageously, the provision of a casing may allow the system to be packaged in a conveniently portable format and may protect the optical components 34 from damage. It will however be understood that in other variants the optical components 34 of the fundus probing assembly 28 may be provided without a casing, for example mounted on an optical table as is well known in the art.

In some implementations, the light source 22 may be integrated into the fundus probing assembly 28. Such an integration may allow the system to have a compact and practical form. For example, in the embodiment of FIG. 1 the light source 22, embodied by a plurality of LED emitters 26, is shown mounted within the casing 36 in a linear arrangement with the optical components of the fundus probing assembly 28, the LED emitters 26 being circularly arranged around an optical axis 38 of the system 20. In other variants, the light source may be offset from the optical axis 38, and the probing light 24 redirected towards the fundus 30 using mirrors or the like. In further variants, one or more optical fibers may be used to carry the probing light 24 at least partially from the light source 22 towards the fundus. It will be further understood that in other implementations the light source 22 may be provided separately from the fundus probing assembly 28. In one example, the fundus probing assembly may include a light port configured to receive the probing light directly or indirectly from the light source, and direct this probing light towards the fundus of the patient's eye.

By way of example only, in the illustrated variant of FIG. 1 the casing 36 of the system 20 has an elongated shape with a circular or other appropriate cross-section. An end wall of the casing at a proximal end proximate the eye of the patient defines an optical window 40 as explained above. Within the casing 36, the fundus probing assembly 28 includes, successively from the proximal end to a distal end:

A focussing lens 34a;

A screen 42 having a hole 44 therethrough aligned with the optical axis 38 and allowing the return light to propagate towards the distal end; as mentioned above, the light source 22 is here embodied by a plurality of LED emitters 26 mounted on the screen 42 on the proximal side thereof and arranged around the hole 44;

A focussing assembly including lenses 34b, 34c, 34d, the middle-placed lens 34c being translatable along the optical axis 38 to adjust the optical focus of the system, and thereby move the image plane 46; actuators allowing the translation of a lens are well known to those skilled in the art and include slider mounts, step motors, cam assemblies, etc.

A collar 48 provides a separation within the casing between the fundus probing assembly 28 and an interface module described further below.

It will be readily understood that the configuration of FIG. 1 and description thereof are provided for illustrative purposes only and that other structural elements and configurations and equivalent thereof may be used to embody all or a portion of the elements of the system without departing from the scope of the invention.

Still referring to FIG. 1, the system 20 further includes an imaging device 50, a spectral analyser 52 and an interface module 54. As explained further below, the imaging device is configured for detecting and displaying the image of the fundus, for example to an operator of the system 20, whereas the spectral analyser 52 is configured to perform the desired spectral analysis on the fundus of the eye.

In some implementations, the imaging device 50 may be embodied by a CCD or CMOS sensor, or any surface that is sensitive that cover light intensity or energy into useful signal. The imaging device 50 may include or be in communication with a processor, computer, circuit or any other hardware component or ensemble of hardware components programmed with instructions for constructing, storing and displaying the images acquired by the imaging device 50. An integrated or separate display may be provided to allow the viewing of the resulting images by an operator or user of the spectroreflectometric system 20.

Figure 7:
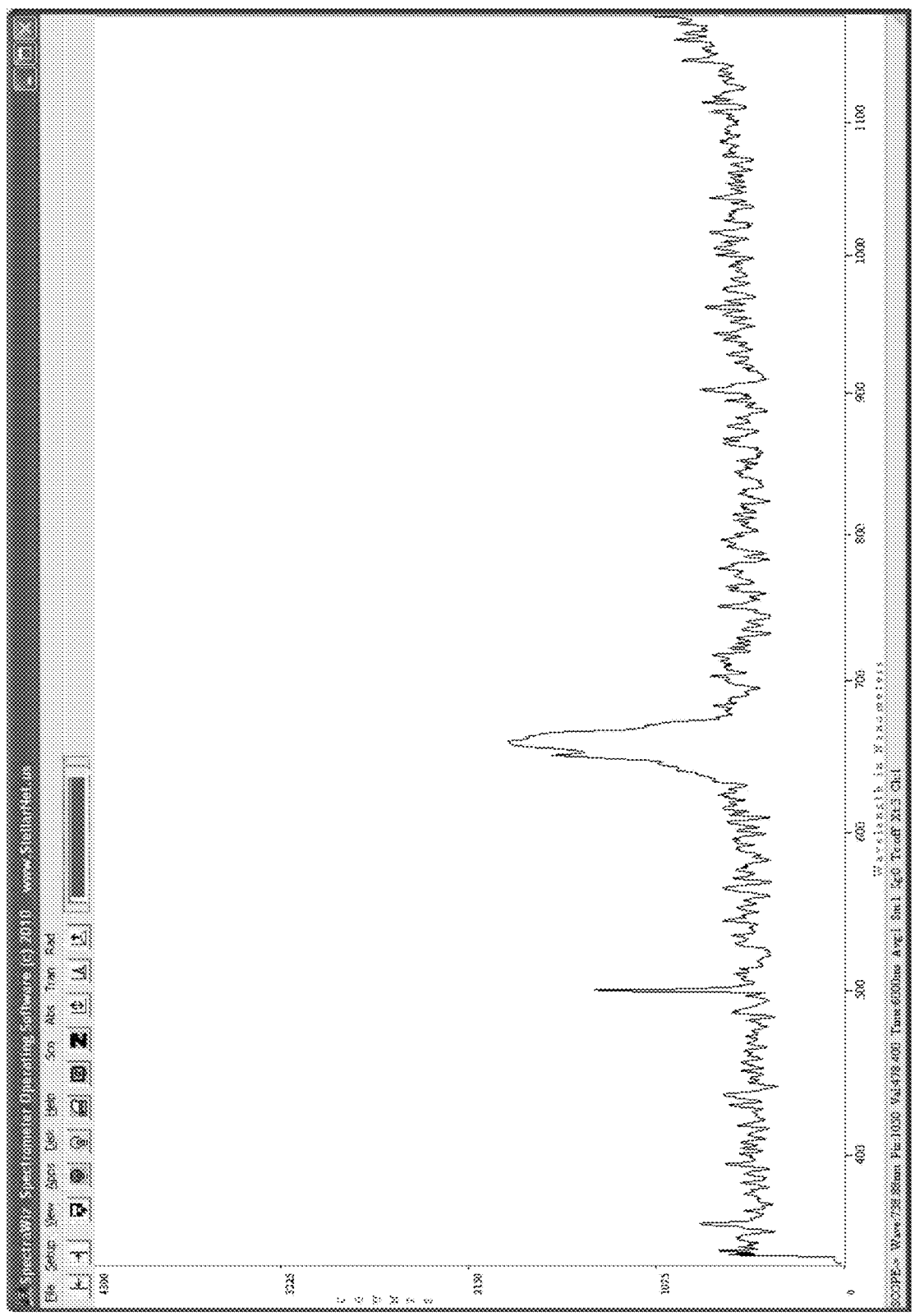
FIG. 7 is an example of a spectrum obtained though a system according to some variants.

The spectral analyser 52 may be embodied by any suitable device allowing an analysis of light as a function of wavelength. The spectral analyser 52 may for example be embodied by an optical spectrometer. As known in the art, optical spectrometers typically decompose incoming light according to its spectrum, typically using light refraction (e.g. in a prism) or light diffraction (in a diffraction grating), and include a detector measuring the distributed intensity of the decomposed light. The spectral analyser may include a computer or processor programmed with instructions to analyse the detected light spectrum in accordance with predetermined parameters, such as explained above. In the illustrated embodiment, the spectral analyser 52 is shown as grating-based, but it will be readily understood that a variety of other configurations and structural components may be used without departing from the scope of the present description. By way of example, the spectral analyser 52 may include at least one dispersive element such as grating in reflection or transmission or a prism. An example of a spectrum obtained through an embodiment of the present description is shown in FIG. 7.

Referring to FIGS. 1 and 1A, as will now be described in more details the interface module 54 is configured to extract a portion of the return light 32 corresponding to region of interest of the fundus of the patient's eye for spectral analysis, while also allowing the operator of the system to visually observe the image of the fundus through the imaging device.

In some implementations, the interface module 54 first includes a sensing interface 56. In some embodiments the sensing interface 56 may be understood as a physical plane where the return light 32 is collected for guidance towards eventual detection by both the imaging device 50 and the spectral analyser 52. The sensing interface 56 extends at the image plane 46 of the fundus 30. As know to those skilled in the optical art, the fundus probing assembly 28 will produce an image of the fundus across one or more image planes depending on the characteristics and configuration of the optical components 34 of the fundus probing assembly 28. The position of the sensing interface 56 is therefore selected so that the return light 32 at the image plane 46 positioned at the sensing interface has a spatial distribution and coherence sufficient to provide a visual representation of the fundus, for eventual detection and display by the imaging device 50.

The interface module 54 is configured to separate the return light at the sensing interface 56 over two different optical paths, a first one for imaging purposes and a second one for spectral analysis.

The interface module 56 includes an optical fiber light collector 58. The optical fiber light collector 58 has a collector input 60 extending along the sensing interface 54 for collecting the return light 32 and a collector output 62 connected to the imaging device 50. One or more optical fiber links 64 carry the collected return light from the collector input 60 to the collector output 62. The return light collected at the collector input therefore provides the image of the fundus to the imaging device 50.

The interface module 56 further includes at least one extraction optical fiber 66. A single such extraction optical fiber 66 is shown in FIGS. 1 and 1A, by way of example, but it will be readily understood that in other embodiments a different number of extraction optical fibers may be provided. Each extraction optical fiber 66 has a fiber input 68 extending at the sensing interface 54 and a fiber output 70 connected to the spectral analyser 52. In accordance with one aspect, the fiber input 68 is integrated into the collector input 60 so as to collect a portion of the return light corresponding to an analysis area within the image of the fundus. In this manner, the portion of the return light collected by the extraction optical fiber is representative of a small area within the image of the fundus which can be characterised via spectral analysis of the corresponding portion of the return light.

Different examples of suitable configurations for the interface module 54 are presented below with reference to FIGS. 2 to 5.

Figure 2:
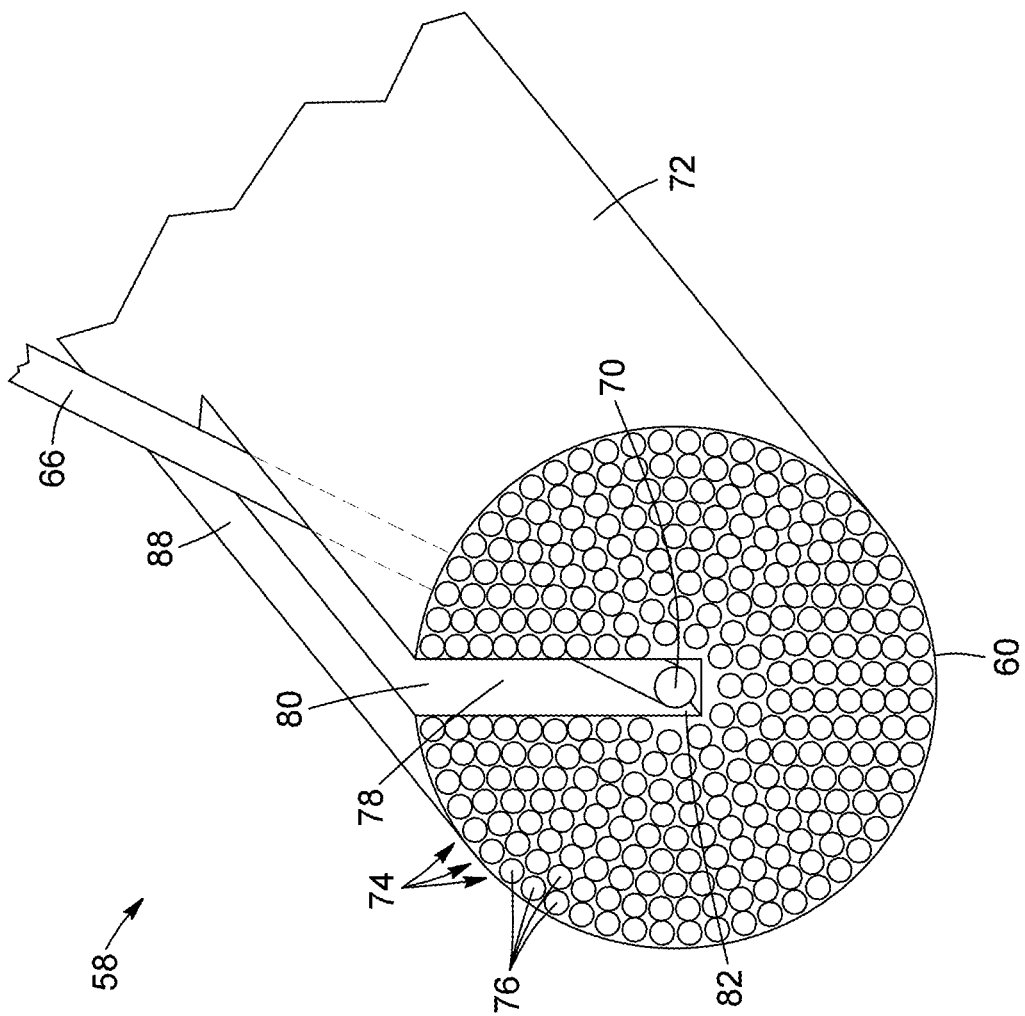
FIG. 2 is a schematized representation of a configuration for an interface module including a plurality of optical fiber links according to one embodiment.

In some implementations, the optical fiber light collector 58 may include a plurality of coherent optical light guides each guiding a segment of the image of the fundus to the imaging device. Referring more particularly to FIG. 2, in one variant the optical fiber light collector 58 may be embodied by an optical fiber bundle 72. As one skilled in the art will readily understand, an optical fiber bundle typically includes several optical fibers "bundled" together that is, assembled such that input light is segmented into corresponding portions individually guided towards the output of the bundle. The optical fibers of a bundle are generally coherent spatially such that an image of the input can be reconstituted at the output. In the variant of FIG. 2, the optical fiber therefore includes a plurality of optical fiber links 74. The optical fiber links 74 have coplanar fiber endfaces collectively defining the collector input 60. It will be understood that in some embodiments the fiber endfaces may define a curved focal plane which may simplify the optical design of the system.

Figure 6:
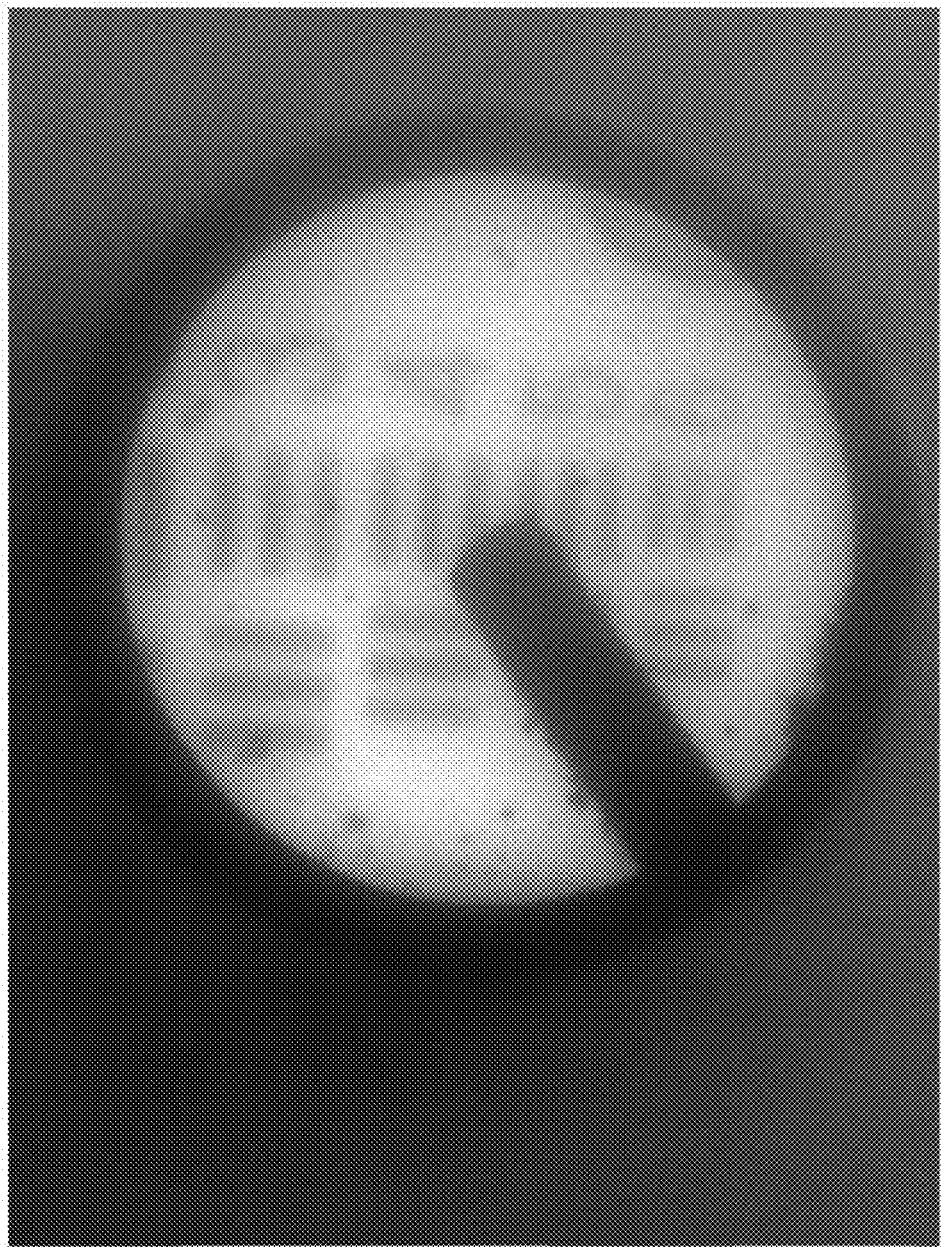
FIG. 6 is an example of an image obtained though a system according to some variants.

In some variations, the collector input 60 includes a slit 78 extending across the fiber endfaces 76 between a peripheral entry point 80 and an interior exit point 82. The extraction fiber 66 lies within the slit 78 with the fiber input 70 projecting through the interior exit point 82 in a coplanar relationship with the fiber endfaces of the optical fiber links. As a result, in one embodiment the resulting configuration provides for the extraction of the return light for spectral analysis from within the image of the fundus. The provision of a slit may lead to a dark line appearing across the image generated by the imaging device, such as for example shown in FIG. 6. For some implementations, this dark line may be non-obstructive enough so as not to interfere with the intended use of the system. In some implementations, the dark line may serve as a visual guide to the alignment of the system with the eye of the patient. In some embodiments, the position of the fiber input 82 of the extraction fiber 66 is central to the collector input 60, as is the case in the variant shown in FIG. 2. It will be readily understood that in other variants the position of the fiber input 82 may be off-center without departing from the scope of the invention. In other variants, the design shown in FIG. 2 may be adapted to include more than one extraction fibers 66 provided through a same or through different slits, and suitable ones of the optical fiber links may be dedicated to the extraction of light.

Figure 3:
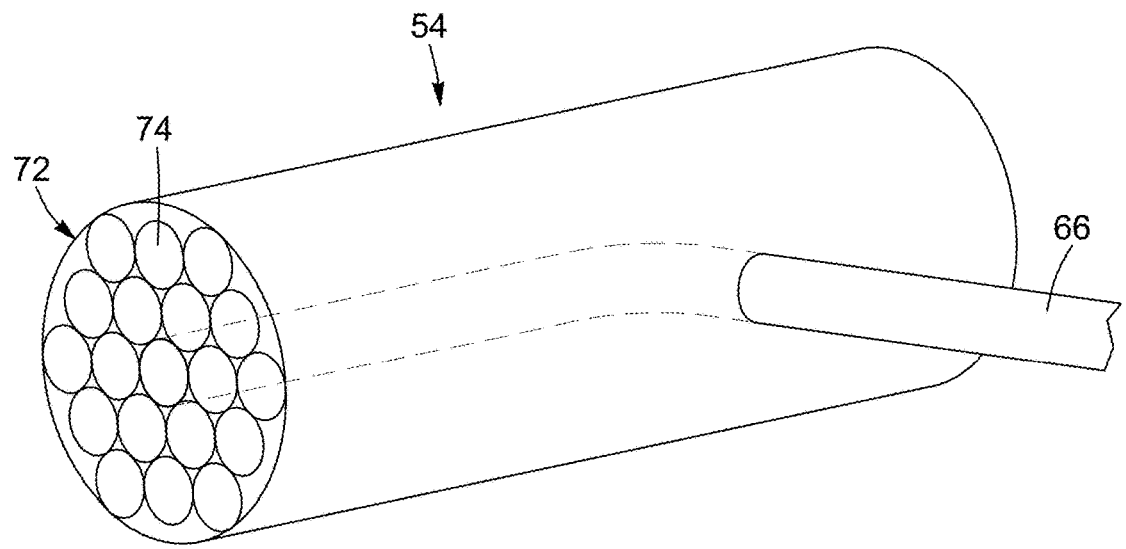
FIG. 3 is a schematized representation of a configuration for an interface module including an optical fiber bundle according to one embodiment.

Referring to FIG. 3, there is shown another variant of the interface module 54. In this variant, the optical fiber light collector is again embodied by an optical fiber bundle 72. However, the extraction fiber 66 of this embodiment corresponds to one of the optical fiber links 74 of the optical fiber bundle 72. This may be achieved by manufacturing a specialized bundle in which individual access to one or more fiber outputs is provided, or by transforming a commercially available for this purpose. In other variants, more than one extraction fiber 66 may be provided, and suitable ones of the optical fiber links dedicated to the extraction of light for spectral analysis. The diameter of the extraction fiber 66 can be equal or different than the optical fiber links 74.

Figure 4:
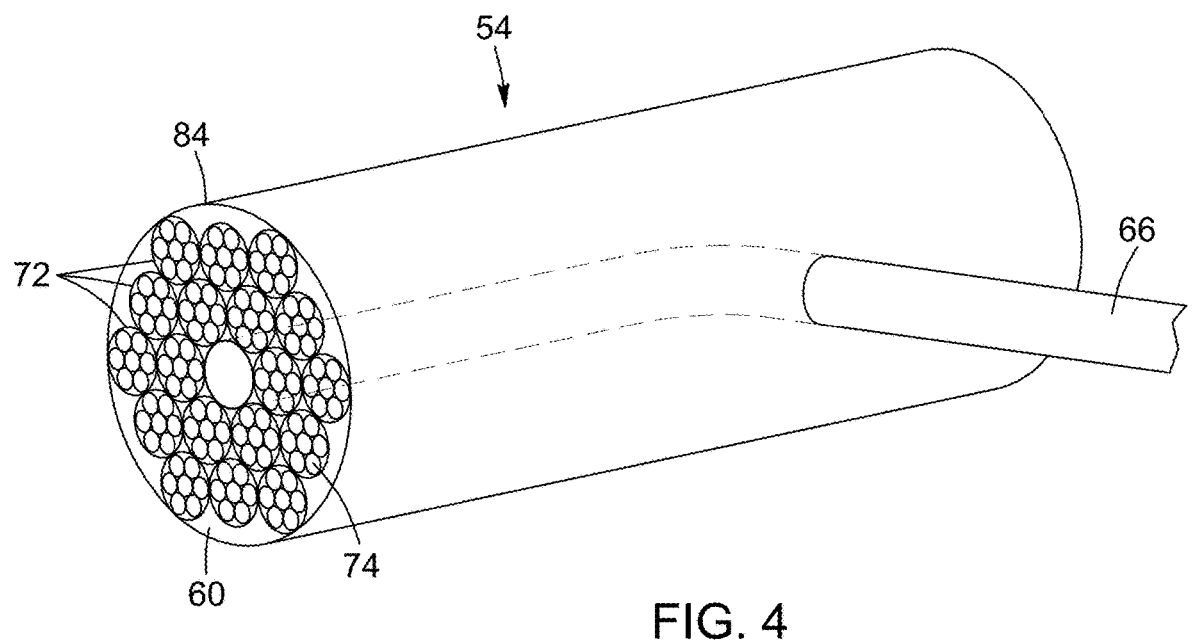
FIG. 4 is a schematized representation of a configuration for an interface module including an optical fiber super-bundle according to one embodiment.

With reference to FIG. 4, there is shown another example of an interface module 54, wherein the optical fiber light collector 58 includes a plurality of optical fiber bundles 72 assembled in a super-bundle 84. Each optical fiber bundle 72 includes a plurality of optical fiber links 74, the optical fiber links of all of said fiber bundles having coplanar fiber endfaces collectively defining the collector input 60. The extraction optical fiber 66 extends within the super-bundle 84, for example through assembly of the individual bundles 72 around the extraction optical fiber. Advantageously, this variant combines the advantage of the segmentation of the fundus image with the ease of assembly of the extraction optical fiber 66 within the optical fiber collector 58.

Figure 5:
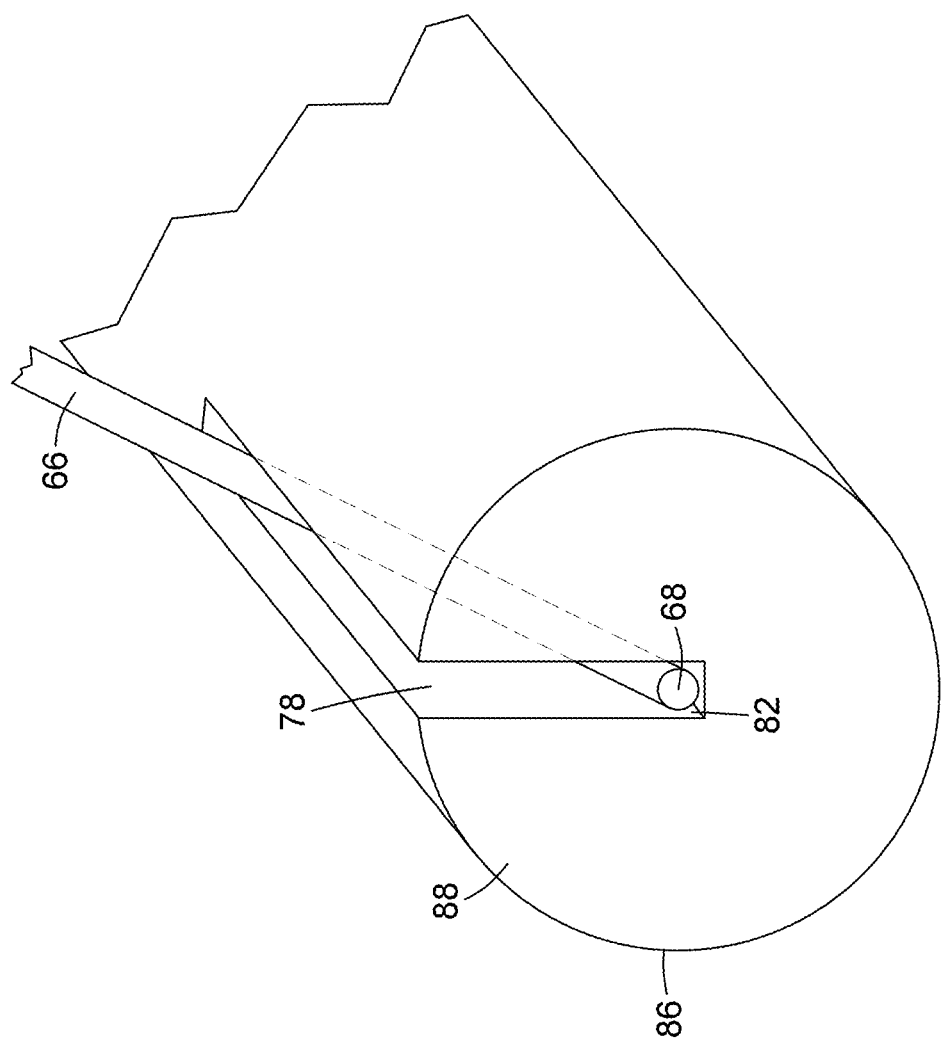
FIG. 5 is a schematized representation of a configuration for an interface module including a large multimode optical fiber according to one embodiment.

Referring to FIG. 5, in yet another variant the optical fiber collector 58 may include a large multimode optical fiber 86 having a fiber endface 88 defining the collector input 60. In this example the collector input 60 may have a slit 78 extending across the fiber endface 88 of the large multimode optical fiber 86 between a peripheral entry point 80 and an interior exit point 82, similarly to the embodiment of FIG. 2. The extraction fiber 66 lies within this slit 78 with the fiber input 68 projecting through the interior exit point 82 in a coplanar relationship with the fiber endface 88 of the large multimode optical fiber 86.

In use, the system 20 described above may be operated as follows. An operator positions and aligns the fundus probing assembly in front of the eye of the patient, as well known in the art. The light source is then activated so that the probing light is projected towards the fundus of the patient's eye, leading to the generation of return light which is collected by the fundus probing assembly, and therefore guided to the interface module. The return light is collected at the sensing interface by both the optical fiber light collector and the extraction fiber. The portion of the light collected by the optical fiber light collector is guided to the imaging device where it is detected and processed. The resulting image of the fundus can then be displayed to the operator, and used as a visual guide to help him or her align the fundus probing assembly with the eye of the patient. The dark spot in the image of the fundus corresponding to the position of the extraction fiber can be moved by the operator until it is over an area of interest within the fundus. Once this alignment is obtained, the light collected by the extraction fiber can be detected an analysed through the spectral analyser as explained above. This operation may be repeated as often as necessary to scan different regions of the fundus as need be.

It will be readily understood that other variations than those described above may be envisioned without departing from the scope of the invention. For example, as mentioned above the system may be used in transmission for the evaluation of tissues other than the eye.

Of course, numerous modifications could be made to the embodiments described above without departing from the scope of the invention as described in the appended claims.

The invention claimed is:

1. A spectroreflectometric system for performing a spectral analysis on the fundus of a patient's eye, comprising:
   a light source generating probing light;
   a fundus probing assembly configured to project the probing light towards the fundus of the patient's eye and to collect return light representative of an image of the fundus;
   an imaging device for detecting and displaying the image of the fundus;
   a spectral analyser configured to perform said spectral analysis; and
   an interface module comprising:
      a sensing interface extending at an image plane of the fundus;
      an optical fiber light collector having a collector input extending along the sensing interface for collecting the return light, and a collector output connected to the imaging device;
      at least one extraction optical fiber, each of the at least one extraction optical fiber having a fiber input extending at the sensing interface and a fiber output connected to the spectral analyser, the fiber input being integrated into the collector input so as to collect a portion of the return light corresponding to an analysis area within the image of the fundus.

2. The spectroreflectometric system according to claim 1, wherein the fundus probing assembly comprises:
   one or more optical components configured to transfer the image of the fundus onto the image plane;
   an assembly of LED emitters defining the light source; and
   a casing enclosing the one or more optical components and the assembly of light emitters.

3. The spectroreflectometric system according to claim 1, wherein the optical fiber light collector comprises a plurality of coherent optical light guides each guiding a segment of the image of the fundus to the imaging device.

4. The spectroreflectometric system according to claim 1, wherein the optical fiber light collector comprises an optical fiber bundle including a plurality of optical fiber links, each of the at least one extraction optical fiber being defined by a corresponding one of the optical fiber links, the optical fiber links having coplanar fiber endfaces collectively defining the collector input.

5. The spectroreflectometric system according to claim 4, wherein the collector interface comprises a slit extending across the fiber endfaces between a peripheral entry point and an interior exit point, the extraction fiber lying within said slit with the fiber input projecting through the interior exit point in a coplanar relationship with the fiber endfaces of the optical fiber links.

6. The spectroreflectometric system according to claim 1, wherein the optical fiber light collector comprises a plurality of optical fiber bundles assembled in a super-bundle, each optical fiber bundle including a plurality of optical fiber links, the optical fiber links of all of said fiber bundles having coplanar fiber endfaces collectively defining the collector input, each of the extraction optical fibers extending within said super-bundle.

7. The spectroreflectometric system according to claim 1, wherein the optical fiber collector comprises a large multimode optical fiber having a fiber endface defining the collector input, and wherein the collector interface comprises a slit extending across the fiber endface of the large multimode optical fiber between a peripheral entry point and an interior exit point, the extraction fiber lying within said slit with the fiber input projecting through the interior exit point in a coplanar relationship with the fiber endface of the large multimode optical fiber.

8. An interface module for use in a spectroreflectometric system for performing a spectral analysis on the fundus of a patient's eye, the system projecting probing light towards the fundus of the patient's eye and collecting return light representative of an image of the fundus, the interface module being positionable at a sensing interface extending at an image plane of the fundus and comprising:
  an optical fiber light collector having a collector input extending along the sensing interface for collecting the return light, and a collector output connectable to an imaging device;
  at least one extraction optical fiber, each of the at least one extraction optical fiber having a fiber input extending at the sensing interface and a fiber output connectable to a spectral analyser, the fiber input being integrated into the collector input so as to collect a portion of the return light corresponding to an analysis area within the image of the fundus.

9. The interface module according to claim 8, wherein the optical fiber light collector comprises a plurality of coherent optical light guides each guiding a segment of the image of the fundus to the imaging device.

10. The interface module according to claim 8, wherein the optical fiber light collector comprises an optical fiber bundle including a plurality of optical fiber links, the optical fiber links having coplanar fiber endfaces collectively defining the collector input.

11. The interface module according to claim 10, wherein the collector interface comprises a slit extending across the fiber endfaces between a peripheral entry point and an interior exit point, the extraction fiber lying within said slit with the fiber input projecting through the interior exit point in a coplanar relationship with the fiber endfaces of the optical fiber links.

12. The interface module according to claim 8, wherein the optical fiber light collector comprises a plurality of optical fiber bundles assembled in a super-bundle, each optical fiber bundle including a plurality of optical fiber links, the optical fiber links of all of said fiber bundles having coplanar fiber endfaces collectively defining the collector input.

13. The interface module according to claim 8, wherein the optical fiber collector comprises a large multimode optical fiber having a fiber endface defining the collector input.

14. The interface module according to claim 13, wherein the collector interface comprises a slit extending across the fiber endface of the large multimode optical fiber between a peripheral entry point and an interior exit point, the extraction fiber lying within said slit with the fiber input projecting through the interior exit point in a coplanar relationship with the fiber endface of the large multimode optical fiber.

15. An interface module for use in a system for performing a spectral analysis on a medium, the system projecting probing light towards the medium and collecting return or transmitted light representative of an image of the medium, the interface module being positionable at a sensing interface extending at an image plane of the medium and comprising:
  an optical fiber light collector having a collector input extending along the sensing interface for collecting the return or transmitted light, and a collector output connectable to an imaging device;
  at least one extraction optical fiber, each of the at least one extraction optical fiber having a fiber input extending at the sensing interface and a fiber output connectable to a spectral analyser, the fiber input being integrated into the collector input so as to collect a portion of the return light corresponding to an analysis area within the image of the medium.

16. The interface module according to claim 15, wherein the optical fiber light collector comprises a plurality of coherent optical light guides each guiding a segment of the image of the medium to the imaging device.

17. The interface module according to claim 15, wherein the optical fiber light collector comprises an optical fiber bundle including a plurality of optical fiber links, the optical fiber links having coplanar fiber endfaces collectively defining the collector input.

18. The interface module according to claim 17, wherein the collector interface comprises a slit extending across the fiber endfaces between a peripheral entry point and an interior exit point, the extraction fiber lying within said slit with the fiber input projecting through the interior exit point in a coplanar relationship with the fiber endfaces of the optical fiber links.

19. The interface module according to claim 15, wherein the optical fiber light collector comprises a plurality of optical fiber bundles assembled in a super-bundle, each optical fiber bundle including a plurality of optical fiber links, the optical fiber links of all of said fiber bundles having coplanar fiber endfaces collectively defining the collector input.

20. The interface module according to claim 15, wherein the optical fiber collector comprises a large multimode optical fiber having a fiber endface defining the collector input, the collector interface comprising a slit extending across the fiber endface of the large multimode optical fiber between a peripheral entry point and an interior exit point, the extraction fiber lying within said slit with the fiber input projecting through the interior exit point in a coplanar relationship with the fiber endface of the large multimode optical fiber.

* * * * *